(12) United States Patent
Marshall et al.

(10) Patent No.: US 9,944,960 B2
(45) Date of Patent: Apr. 17, 2018

(54) PROCESS FOR MICROBIAL PRODUCTION OF DIHYDROLIPOIC ACID AND EXTRACTION OF DIHYDROLIPOIC ACID WITH EDIBLE OILS

(71) Applicant: Premier Research Labs, LP, Austin, TX (US)

(72) Inventors: Robert J. Marshall, Round Rock, TX (US); Nickolas Labinsky, Pflugerville, TX (US); Lindsey Dunham, Austin, TX (US); Michael Ratkovich, Austin, TX (US); Walter Trikosko, Austin, TX (US)

(73) Assignee: Premier Research Labs, LP, Austin, TX (US)

( * ) Notice: Subject to any disclaimer, the term of this patent is extended or adjusted under 35 U.S.C. 154(b) by 0 days.

(21) Appl. No.: 14/943,185

(22) Filed: Nov. 17, 2015

(65) Prior Publication Data

US 2017/0137852 A1    May 18, 2017

(51) Int. Cl.
  *C12P 11/00* (2006.01)
  *C11B 3/00* (2006.01)
  *A23L 1/30* (2006.01)

(52) U.S. Cl.
  CPC ............. *C12P 11/00* (2013.01); *A23L 1/3006* (2013.01); *C11B 3/003* (2013.01); *C11B 3/006* (2013.01); *A23Y 2220/17* (2013.01)

(58) Field of Classification Search
  None
  See application file for complete search history.

(56) References Cited

U.S. PATENT DOCUMENTS

| | | | |
|---|---|---|---|
| 6,906,210 B2 | 6/2005 | Klatt et al. | |
| 7,109,362 B2 | 9/2006 | Klatt et al. | |
| 8,304,217 B2 | 11/2012 | Marshall | |
| 8,530,209 B2 | 9/2013 | Marshall | |
| 2006/0234359 A1 | 10/2006 | Dassler | |
| 2011/0262976 A1 | 10/2011 | Kandula et al. | |

FOREIGN PATENT DOCUMENTS

DE    WO2005014570 A1    2/2005

OTHER PUBLICATIONS

Singh et al. Curr Protein Pept Sci. 2017, 18, 1-11.*

* cited by examiner

*Primary Examiner* — Christian Fronda
(74) *Attorney, Agent, or Firm* — Amin Talati Upadhye LLP; George M. Carrera, Jr.

(57) ABSTRACT

A process for production and extraction of dihydrolipoic acid (DHLA) relates to the biotransformation of R-lipoic acid to dihydrolipoic acid. The process ferments the lipoic acid with bacteria selected from the genus of any of the following bacteria: *Lactobacillus, Enterococcus, Pediococcus,* or *Bacillus*. More particularly the present invention relates to a method for the extraction of DHLA utilizing a non-traditional solvent system, namely a food oil. Generally the DHLA that is produced in the present method is isolated from cells which have been inactivated or killed.

8 Claims, 5 Drawing Sheets

A - Manhole Lid
B - pH Meter
C - RTD Heating Control Temperature Unit
D - Not In use
E - Mixed Gas Input
F - Sampling Port
G - Motor
H - iSense Biogas Meter
I - Not In Use
J - Dickson One Temperature Probe
K - Not In Use
L - Exhaust Gas

PROCESS FOR MICROBIAL PRODUCTION OF DIHYDROLIPOIC ACID AND EXTRACTION OF DIHYDROLIPOIC ACID WITH EDIBLE OILS

TECHNICAL FIELD

The present invention relates to the biotransformation of R-lipoic acid to dihydrolipoic acid (DHLA). The process ferments the lipoic acid with bacteria selected from the genus of any of the following bacteria: *Lactobacillus, Enterococcus, Pediococcus*, or *Bacillus*. More particularly the present invention relates to a method for the extraction of DHLA utilizing a non-traditional solvent system, namely a food oil. Generally the DHLA that is produced in the present method is isolated from cells which have been inactivated or killed.

BACKGROUND

Dihydrolipoic acid is a valuable nutrient substance. Its production and isolation is made difficult due to the ease of oxidation to its disulfide form, namely, lipoic acid, under various standard conditions.

DHLA is typically produced within the body through the redox conversion of lipoic acid or alpha-lipoic acid (ALA) during normal metabolic activity. However, the body generally only produces an amount of DHLA sufficient to assist in metabolic function. However, DHLA has been shown, at least in part, to be an effective antioxidant and chelating agent that can be utilized to scavenge reactive nitrogen species (RNS) and reactive oxygen species (ROS) such as, for example, singlet oxygen, that can contribute to a number of degradative pathological syndromes such as diabetes, glaucoma, atherosclerosis, and other neuropathies. DHLA has also been found, at least in part, to be effective to prevent or repair oxidative damage in cells and to regenerate certain important nutrients in the body such as, for example, vitamins C and E. However, there is no DHLA commercially available; only ALA which is derived from non-living sources which have no DNA and may induce cellular DNA degradation especially in long term use. As a result it is believed that such ALA used in the cell to make minimal amounts of DHLA is not beneficial for long term use. Conversely, DHLA derived from once living sources includes DNA which is known to support cell DNA. In U.S. Pat. No. 8,530,209 to Marshall, stabilized dihydrolipoic acid (DHLA) for use in a medicament or nutritional supplement is derived from a once living source. In particular, the stabilized DHLA compound can be derived from a microbiological culture media including at least one live probiotic organism, R-lipoic acid, and at least one nutraceutical or nutritive agent.

It is evident that there is difficulty in isolating and/or stabilizing large quantities of DHLA. For natural sources, relatively small amounts can be isolated in vivo, as discussed above. However, if a way could be found to prepare and isolate larger quantities of DHLA in situ, this would represent a valuable contribution to the nutraceutical and medical arts.

SUMMARY

This invention relates to biotransformation of lipoic acid to dihydrolipoic acid (DHLA) utilizing bacteria.

A general object of the invention is to provide a method for producing beneficial compounds including DHLA, or a salt thereof, for use in a medicament or a nutritional supplement.

In an embodiment, a method for producing DHLA is described herein including dispersing a microbiological culture media including at least one live probiotic organism, R-lipoic acid, and/or at least one nutritive agent in distilled water to form a broth, incubating the broth at a predetermined temperature for a select period of time to induce probiotic activity; optionally adding organic ethanol to halt the probiotic activity, and separating the desired compound from the broth by means of olive oil extraction.

In another embodiment a process for the production of dihydrolipoic acid (DHLA), or a salt thereof, is described, comprising the steps of:

(a) preparing a microbiological culture comprising at least one species of *Lactobacillus* spp., *Enterococcus* spp., *Pediococcus* spp., or *Bacillus* spp.;

(b) treating an aqueous broth containing molasses, N-acetyl-L-cysteine, rice protein, nutritional yeast, sugar, one or more mineral salts, one or more nucleotides, and a first edible oil with the microbiological culture to form a microbial broth;

(c) incubating the microbial broth at a temperature of about 35° C. to about 40° C. for at least about 48 hours;

(d) feeding the microbial broth with R-lipoic acid, turmeric rhizome, N-acetyl-L-cysteine, glutathione, L-arginine, and NADH;

(e) adjusting the pH to about 8.0;

(f) incubating the microbial broth for at least about 10 days;

(g) optionally feeding the microbial broth after the at least 12 days with molasses, rice protein, nutritional yeast, and natamycin;

(h) optionally adjusting the pH to about 8.0;

(j) incubating the microbial broth from at least about 2 days to about 9 days;

(k) adjusting the pH to about 2.0;

(l) adding a second edible oil in a volume of about 60-100% total microbial broth volume, and water in a volume of about 100% total microbial broth volume to form two layers;

(m) mixing the edible oil layer and the aqueous layer to effect extraction of DHLA, or a salt thereof, into the edible oil layer; and (n) separating the edible oil layer containing DHLA, or a salt thereof.

DETAILED DESCRIPTION

Figure 1:
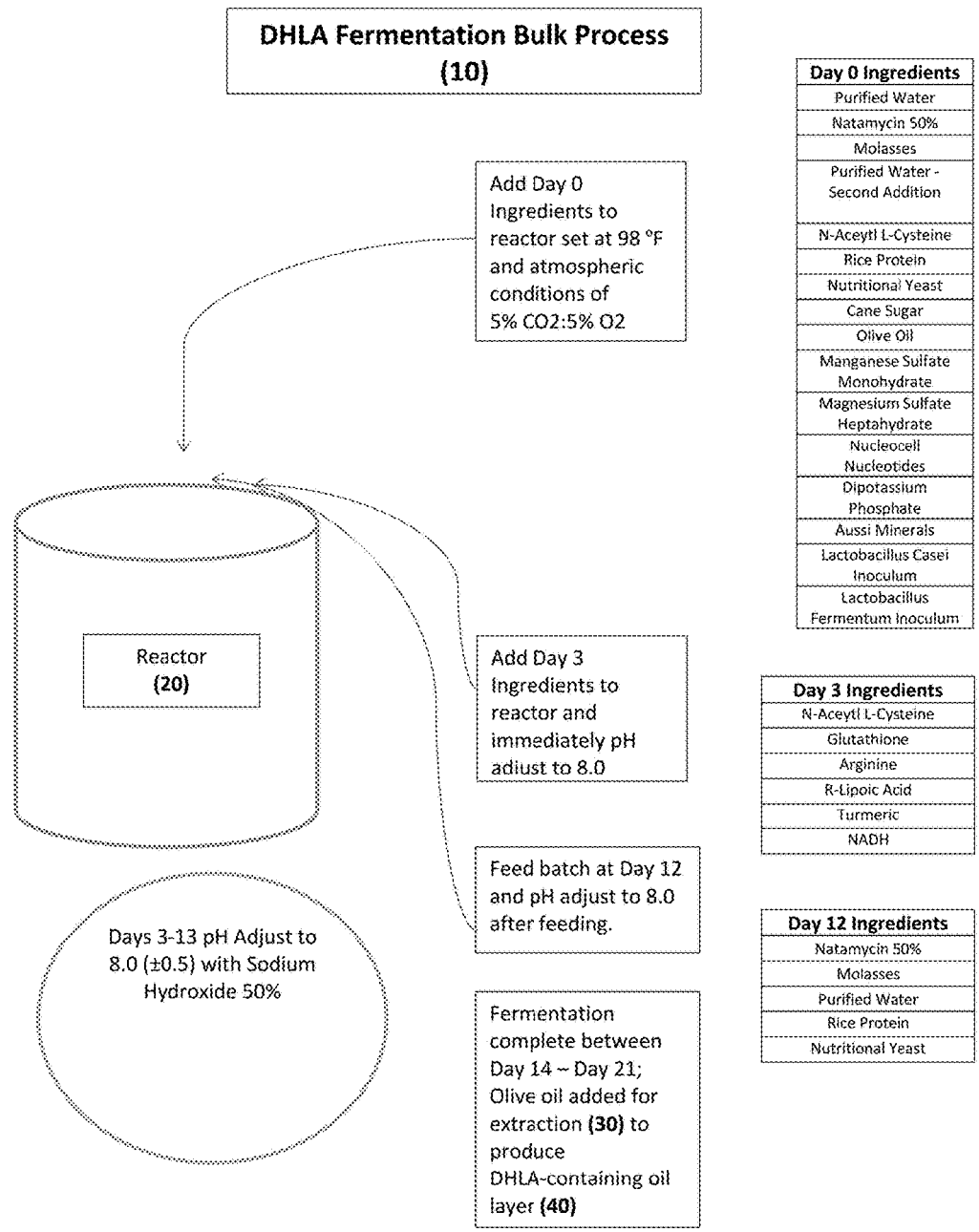
FIG. 1 depicts a schematic of one embodiment of a bulk fermentation process performed in batch mode for the production of DHLA contained in an oil layer.

Over the past few decades the medical, pharmaceutical and nutritional industries have demonstrated an increased interest in the use of traditional herbal and/or homeopathic medicines for the treatment and/or prevention of a variety of diseases, as well as for maintenance of good health and bodily function. Advances in the fields of biology, chemistry and medicine have allowed researchers to more closely and accurately study the impact and effects of various compounds on the human body and its myriad of metabolic and physiological processes. Such advances have led to an improved understanding of the uptake of many compounds such as, for example, nutrients, vitamins, minerals and other naturally occurring or synthetic compounds, and the role these compounds play in the day to day functioning of the body.

One area of study has focused on understanding the physiological effects of "reactive oxygen species" (ROS). ROS are byproducts of the normal metabolic processes of living organisms. ROS include oxygen-derived free radicals and non-radical derivatives that can cause oxidative damage to biological structures. ROS have also been shown to play a role in the aging process and a number of pathological syndromes such as, for example, diabetes. However, oxidative damage caused by ROS can be reduced or prevented through a number of mechanisms such as, for example, the use of antioxidants that can react directly with ROS in the body.

While various nutraceutical or nutritive agents can be utilized in the microbiological culture media of the invention, suitable nutraceutical or nutritive agents should contribute to the production of the desired beneficial compound as well as to the stability of the microbiological media. The particular nutraceutical or nutritive agent or agents utilized in the microbiological culture media will depend upon the beneficial compound to be derived. For example, if the beneficial compound to be derived from the microbiological culture media is stabilized dihydrolipoic acid (DHLA), the nutritive agent contained in the microbiological media may be tumeric rhizome (*curcuma longa*). In another preferred embodiment, the nutraceutical or nutritive agent utilized in the microbiological culture media may be a synthetic form or precursor of the beneficial compound to be derived or may be a naturally occurring source of the beneficial compound, such as, for example, a plant or herb, which must be processed in order to isolate the beneficial compound.

Possible uses for DHLA include as a nutraceutical or active pharmaceutical ingredient (API) in neutralizing free radicals, preventing them from causing harm. It directly destroys damaging superoxide radicals, hydroperoxy radicals and hydroxyl radicals. It has been shown in vitro that dihydrolipoate (DL-6,8-dithioloctanoic acid) has antioxidant activity against microsomal lipid peroxidation. Dihydrolipoate is tested for its neuroprotective activity using models of hypoxic and excitotoxic neuronal damage in vitro and rodent models of cerebral ischemia in vivo. Dihydrolipoate, similarly to dimethylthiourea, is able to protect neurons against ischemic damage by diminishing the accumulation of reactive oxygen species within the cerebral tissue.

The process as described herein provides a way to produce large quantities of DHLA in a relatively short amount of time. Further, the extraction method provides a way to extract out the DHLA and lipoic acid without conventional solvents normally used in extraction process. This process leaves no solvent residue which would normally be present in the final product of all solvent extraction processes.

In one aspect the process in it principal embodiment contains the following ingredients to produce DHLA in situ. With this formula, the conversion ratio is not as high as other exemplary methods, and the amount of time it takes to reach peak conversion is longer than 21 days.

*Lactobacillus fermentum*
R-Lipoic Acid
Turmeric (rhizome source)
N-Acetyl L Cysteine
NADH
Molasses
RO Water
Sodium Hydroxide
Hydrochloric acid
Olive Oil
Rice Protein
Yeast Flakes
Organic cane sugar
Manganese Sulfate
Magnesium Sulfate
Dipotassium Phosphate
Natamycin Generally solvent systems that dissolve R-lipoic acid can be used to extract out DHLA. However solvents that are immiscible with water are preferred to avoid extracting out the water soluble components, or at least minimizing co-extraction of such components. The bacteria used also can be altered. Most bacteria produce DHLA. The bacterial species described herein and listed are some of the most efficient when used in DHLA production, for example, and produced the largest yield.

In another embodiment, the following ingredients are used to produce DHLA on a large scale in situ.

*Lactobacillus fermentum*
*Lactobacillus casei*
R-Lipoic Acid
Turmeric
Glutathione
N-Acetyl L Cysteine
L-Arginine
NADH
Molasses
RO Water
Sodium Hydroxide
Hydrochloric acid
Olive Oil
Rice Protein
Yeast Flakes
Organic cane sugar (as sucrose)
Manganese Sulfate
Magnesium Sulfate
Dipotassium Phosphate
Natamycin Nucleocell Nucleotides are available from Future Food, Santa Rosa, Calif.

Aussi/Aussie Minerals are available from Symbio Alliance, Eight Mile Plains, Q4113, Australia.

Natamycin 50% is available from ProFood International, Inc., Lisle, Ill.

A useful olive oil for the extraction is Cibaria Moroccan Olive Oil, Riverside, Calif.

Alternatively, other natural oils may be used in the present process for the purpose of DHLA extraction. Suitable oils include edible oils, including food or vegetable oils that may be used in embodiments of the process, and also include, but are not limited to, grape seed oil, sesame oil, borage oil, fish oil, sea buckthorne oil, flax oil, coconut oil, peanut oil, canola oil, jojoba oil, corn oil, palm oil, evening primrose oil, amaranth oil, safflower oil, soybean oil, sunflower oil, palm oil, cotton seed oil, almond oil, cashew oil, hazelnut oil, macadamia oil, pecan oil, pistachio oil, walnut oil, acai oil, blackcurrant oil, apricot oil, argan oil, artichoke oil, avocado oil, babassu oil, ben oil, borneo tallow nut oil, buffalo gourd oil, carob pod oil, coriander seed oil, false flax oil, hemp oil, kapok seed oil, lallemantia oil, meadowfoam seed oil, mustard oil, okra seed oil, *perilla* seed oil, pequi oil, pine nut oil, poppy seed oil, prune kernel oil, pumpkin seed oil, *quinoa* oil, ramtil oil, rice bran oil, tea oil, thistle oil, and wheat germ oil. Additionally, isoamyl acetate may be used as an extractant in the process.

One or more edible oils may be used in the production process for the biotransformation of lipoic acid to DHLA. The first edible oil and the second edible oil can be the same or different, and the edible oil is selected from the group consisting of food oil, vegetable oil, botanical oil, grape seed oil, sesame oil, borage oil, fish oil, sea buckthorne oil, flax oil, coconut oil, peanut oil, canola oil, jojoba oil, corn oil, palm oil, evening primrose oil, amaranth oil, safflower oil, soybean oil, sunflower oil, palm oil, cotton seed oil, almond oil, cashew oil, hazelnut oil, macadamia oil, pecan oil, pistachio oil, walnut oil, acai oil, blackcurrant oil, apricot oil, argan oil, artichoke oil, avocado oil, babassu oil, ben oil, borneo tallow nut oil, buffalo gourd oil, carob pod oil, coriander seed oil, false flax oil, hemp oil, kapok seed oil, lallemantia oil, meadowfoam seed oil, mustard oil, okra seed oil, *perilla* seed oil, pequi oil, pine nut oil, poppy seed, prune kernel oil, pumpkin seed oil, *quinoa* oil, ramtil oil, rice bran oil, tea oil, thistle oil, and wheat germ oil.

Biotransformation is carried out in a fermentation process for the production of DHLA, using lipoic acid as a feedstock. It is understood that the microbiological culture contains bacterial cells of one or more species as described. The microbiological culture is used to prepare a microbial broth containing yeast.

As a general principle, the broth provided by the above list of ingredients contains several unexpected advantages and beneficial properties. Without being bound by theory, the fermentation broth includes the following properties in terms of one or more of the components. The rice protein and L-Cysteine (i.e., in the form of N-acetyl-L-cysteine) each may provide nitrogenous and carbonaceous compounds. Yeast flakes provide essential B-Vitamins and organic cane sugar (sucrose) is the fermentable carbohydrate and energy source. Olive oil (broth portion) supplies oleic acid and other fatty acids required for metabolism of Lactobacilli. Magnesium sulfate and manganese sulfate provide essential ions for multiplication of Lactobacilli. Phosphate salt provides good buffering action. Natamycin prevents mold and yeast growth. Glutathione, L-arginine, N-acetyl L-cysteine and NADH are growth promoters and reducing agents. Turmeric can prevent R-Lipoic acid (as starting material feedstock) from polymerizing. Nucleotides are utilized as a growth factor(s). Aussie minerals can provide essential minerals. Molasses provides additional growth factors for the *Lactobacillus* organisms.

The methods described above may be further understood in connection with the following Examples. In addition, the following non-limiting examples are provided to illustrate the invention.

EXAMPLE 1

DHLA Bulk Fermentation Process (Batch mode)

(1) A 48 hour inoculation culture is prepared from the stock culture of L. *Casei* and L. *Fermentum* as follows.

(1a) *Lactobacillus Casei* Inoculum Preparation:

The *Lactobacillus casei* inoculum was prepared 48 hours prior to the mixing start date. Ten (10) grams of raw material (0022) Freeze-dried 10 billion CFU/g *Lactobacillus casei* from Nebraska Cultures, Inc. was added to 500 mL of MRS Broth supplied by Edge Biologicals, Inc. Catalog No. B-0965 Memphis, Tenn. The inoculum incubated at 37° C. with an atmosphere of 90% N2: 5% CO2: 5% O2. After the 48 hour incubation, the 500 mL inoculum was washed twice with phosphate buffer using the centrifuge. The washed pellets were then reconstituted with a total of 100 mL phosphate buffer and were combined into one container to inoculate the DHLA Fermentation bulk batch.

(1b) *Lactobacillus Fermentum* Inoculum Preparation:

The *Lactobacillus fermentum* inoculum used was isolated from kefir. The glycerol stock culture created followed the Stock Culture Program work instruction FM9802-11. This inoculum was prepared 48 hours prior to the mixing start date. One scrape of the L. *fermentum* glycerol stock (Lot#2014-30.04) was added to 500 mL of MRS Broth supplied by Edge Biologicals, Inc. Catalog No. B-0965 Memphis, Tenn. The inoculum incubated at 37° C. with an atmosphere of 90% N2: 5% CO2: 5% O2. After the 48 hour incubation, the 500 mL inoculum was washed twice with phosphate buffer using the centrifuge. The washed pellets were then reconstituted with a total of 100 mL phosphate buffer and were combined into one container to inoculate the DHLA Fermentation bulk batch.

(2) The inoculation culture is washed twice. Washing involves centrifuging the cells, decanting the supernatant, and then immersing the cells in RO water.

(3) The media is prepared by mixing molasses (14 kg) in PRL broth (as in Table 1 below) and inoculating with the cell cultures of step (2) ("the inoculum"). This media is within a culturing system that allows for interval agitation in the reactor described below. The interval settings are 3 minutes at 150 RPM and a 1 minute rest. Therefore, the above ingredients are added to the reactor set to 98° F. and atmospheric conditions of 5% $CO_2$:5% $O_2$:90% $N_2$.

TABLE 1

| Item Name | Source | Amount Used |
|---|---|---|
| N-Acetyl L-Cysteine | Amazon Forest | 350.0 g |
| Brown Rice Protein 80% | Axiom Foods | 7.0 Kg |
| Nutritional Yeast | Amcor Rigid Plastics USA, Inc. | 7.0 Kg |
| Molasses | Wholesome Sweeteners | 14.0 Kg |
| Cane Sugar | Amazon Forest | 6.3 Kg |
| Nucelocell Nucleotides | Future Foods | 1.4 Kg |
| Olive Oil | Cibaria | 700.0 g |
| Manganese Sulfate Monohydrate | Jost Chemical CO. | 39.2 g |
| Magnesium Sulfate Heptahydrate | Jost Chemical CO. | 143.4 g |
| Aussi Mineral Liquid | Symbio Alliance | 1.1 Kg |
| Dipotassium Phosphate | ProFood International, Inc. | 1.4 Kg |

TABLE 1-continued

| Item Name | Source | Amount Used |
|---|---|---|
| Natamycin 50% | ProFood International, Inc. | 25.2 Kg |
| Water, Purified | In House | 331.0 Kg |
| *Lactobacillus Casei* Inoculum | Nebraska Cultures | 1 ea., as above |
| *Lactobacillus Fermentum* Inoculum | In House Kefir Isolate | 1 ea., as above |

Figure 2A:
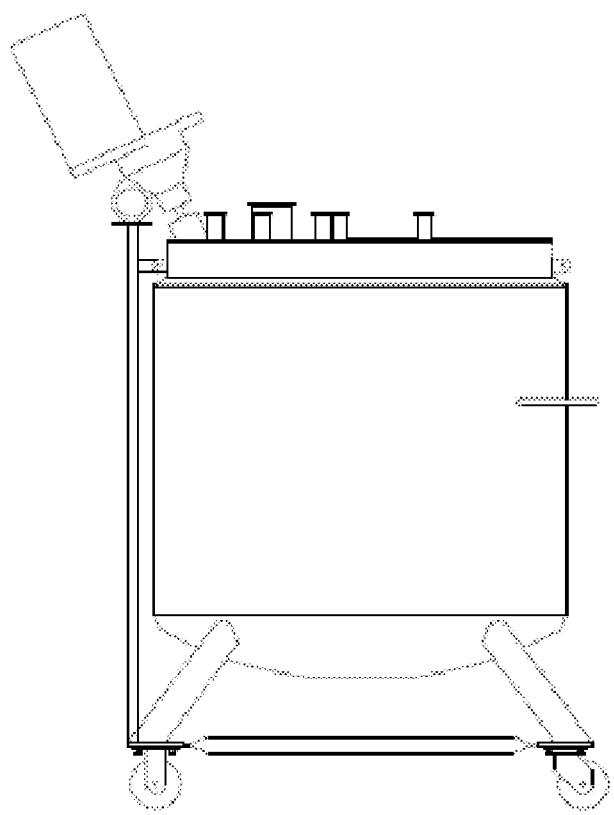
FIG. 2A depicts in one embodiment a representative reactor on a skid, used in accordance with the principles of the bulk fermentation process.
Figure 2B:
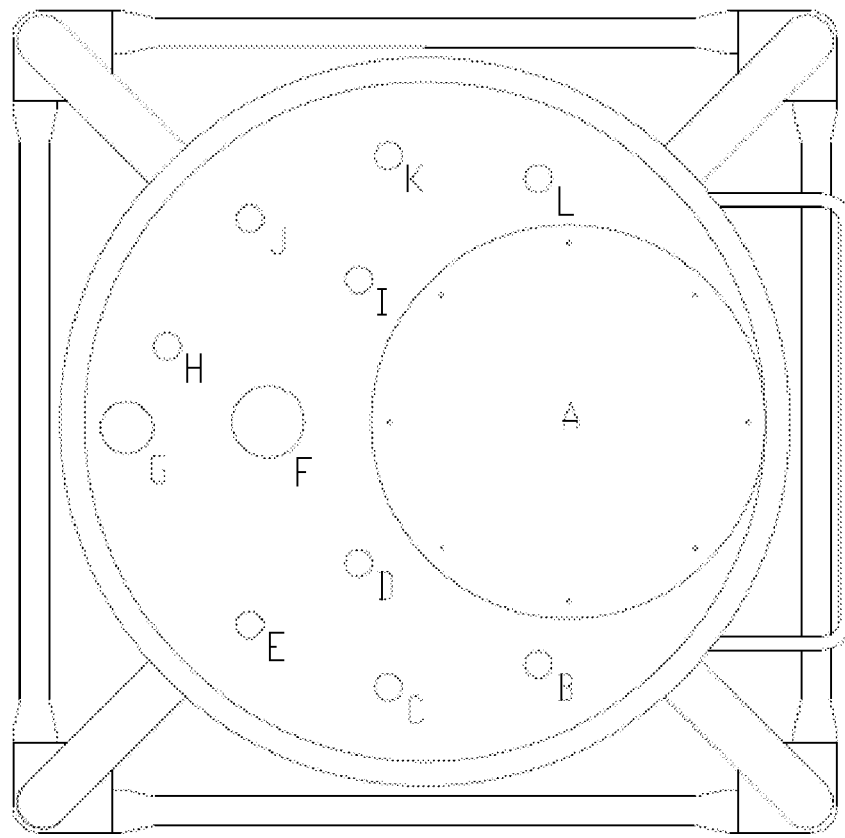
FIG. 2B depicts a top view of the reactor skid of FIG. 2A, showing various exemplary ports for use in the bulk fermentation process. The port layout and descriptions of each port is shown.

Reactor and equipment (see also FIGS. 2A and 2B).

All modifications to the stainless steel DCI 150 gallon reactor were accomplished in-house by the maintenance department. Seven out of eleven ports available on the vessel were utilized in order to create the required atmosphere and acquire all data pertinent to this process. The ability of having an air tight sealed vessel is essential for regulating the atmosphere. The schematics of the vessel are shown in FIG. 2A.

The port layouts and descriptions of each port are defined in FIG. 2B. All pH readings were done with an Accumet Ab15 pH meter that was calibrated daily. The flow-thru monitoring pH electrode from Hannah Instruments was used as a secondary aid to measure the real time pH inside the vessel during the adjustment procedure. All temperature readings were measured using a data probe from Dickson with live access to temperature readings online. The temperature range for this project was 85-105° F. All atmosphere conditions were monitored using the iSense Carbon Dioxide, Oxygen Biogas Meter & Sampling Data Logger. Table 2 describes each vendor and part number for all parts used to modify the vessel.

Thus, the equipment that was used to enhance the reactor and acquire data is listed in Table 2.

TABLE 2

| Source | Part No. | Description |
|---|---|---|
| DCI | 96-PH-53798 | 150 Gallon Portable Reactor |
| Praxair | PRS 30021331570 | Oxygen Regulator |
| Praxair | PRS 30021531320 | Carbon Dioxide Regulator |
| Praxair | PRS 502S1332-580 | ProStar SS Manifold Station |
| Cole-Parmer | T-03214-36 | Multitube Gas Flowmeter Frame |
| Cole-Parmer | T-32047-04 | Carbon Dioxide Flow Tube 0-1 LPM |
| Cole-Parmer | T-32047-20 | Nitrogen Flow Tube 0-12 LPM |
| Cole-Parmer | T-32042-26 | Oxygen Flow Tube 0-1 LPM |
| Cole-Parmer | T-03218-67 | High Resolution Valve Cartridge 201-100 mL/min × 2 units |
| Cole-Parmer | T-03218-70 | High Resolution Valve Cartridge 6201+ mL/min |
| McMaster-Carr | 3184K7 | Crush-Resistant White Silicone Rubber Tubing × 25' |
| Cole-Parmer | T-06490-17 | Bev-A-Line IV Tubing 3/8" ID × 50' |
| Cole-Parmer | T-06490-19 | Bev-A-Line IV Tubing 1/2" ID × 50' |
| CO2Meter.com | CM-0200 | iSense Carbon Dioxide, & Oxygen Biogas Meter & Sampling Datalogger |
| CO2Meter.com | DAS0100 | Data Acquisition Software |
| Hannah Instruments | HI 1001 | Flow-thru Monitoring pH Electrode |
| Hannah Instruments | BL 931700 | pH Mini Controller |
| Dataq Instruments | EL-USB-4 | Current Loop Data Logger |
| Lascar | EL-WIN-USB | Easy Log Software |
| Dickson | 14240101 | Temperature Probe and Data Logger |
| McMaster-Carr | 38705K38 | RTD Probe |
| McMaster-Carr | Various | Food & Beverage White Nylon Barbed Tube Fittings |

(4) On day 3: R-Lipoic Acid, Turmeric, N-Acetyl L-cysteine, Glutathione, L arginine and NADH are added to the batch as in Table 3.

TABLE 3

| Item Name | Source | Amount Used |
|---|---|---|
| R-Lipoic Acid | Watson Industries, Inc. | 8.75 Kg |
| Turmeric | Jiaherb | 9.63 Kg |
| NADH | Maypro Industries, LLC. | 350.0 g |
| N-Acetyl L-Cysteine | Amazon Forest | 3.5 Kg |
| Glutathione | GWI | 3.5 Kg |
| L-Arginine | Chementry Industries Inc. | 3.5 Kg |

(5) The batch is pH adjusted within 10 minutes using 50% sodium hydroxide to a pH of 8.0 and then kept at 37° C. at an atmosphere of 5% $O_2$ and 5% $CO_2$.

(6) The batch is fermented for 14-21 days (inclusive of steps 7 and 8). Note: during the process on days 3-13 the pH is adjusted to 8.0 (+/−0.5) with 50% sodium hydroxide.

(7) Beginning on day 3 the batch is pH adjusted daily from an Acidic pH to a pH of 8.0 with Sodium Hydroxide. Once a pH of 8 is reached and maintained the adjustments are halted, and reinitiated as necessary.

(8) On day 12: the batch is fed with molasses, rice protein, yeast flakes and Natamycin (50%), in water, as in Table 4. Also, the pH is re-adjusted to 8.0 again after this feeding.

TABLE 4

| Item Name | Source | Amount Used |
|---|---|---|
| Brown Rice Protein 80% | Axiom Foods | 1.75 Kg |
| Nutritional Yeast | Amcor Rigid Plastics USA, Inc. | 1.75 Kg |
| Molasses | Wholesome Sweeteners | 1.75 Kg |
| Natamycin 50% | ProFood International, Inc. | 12.5 g |
| Water, Purified | In House | 1.0 Kg |

(9) Once fermentation is complete and the batch reaches NLT 70% conversion (as demonstrated below), the batch is pH adjusted with hydrochloric acid to a pH of 2.0. Generally the fermentation is complete between days 14 and 21. In one preferred embodiment, the fermentation is complete after about 14 days.

(9a) HPLC Protocol for Analysis of DHLA

Samples were collected daily, beginning at day 3, to monitor DHLA conversion using HPLC-UV Vis diode array analysis on a Dionex Chromeleon 7 Network HPLC System. Table 5 defines all reagents and standards used and Table 6 defines all general equipment and supplies used for the HPLC analysis.

TABLE 5

| Reagent | Chemical purity grade |
|---|---|
| Phosphoric Acid, 85% | HPLC grade or better |
| Water (H2O) | HPLC grade or better |
| Acetonitrile (ACN) | HPLC grade or better |

TABLE 5-continued

| Reagent | Chemical purity grade |
|---|---|
| Glutathione | Raw material |
| N-acetyl L-cysteine | Raw material |
| Alpha lipoic acid | Analytical reference standard |
| Dihydrolipoic acid | Analytical reference standard |

TABLE 6

| Component | Description or Part No. |
|---|---|
| Pipet | 2 mL, or 1-5 mL adjustable |
| Syringe filters | 25 mm Nylon or PVDF |
| Laboratory glassware | Miscellaneous Class A |
| Microbalance with | Mettler Toledo UMX2 or equivalent |
| Analytical balance | Denver Instruments SI-234 or equivalent |
| HPLC System | Thermo Scientific Dionex Ultimate 3000 with photodiode |
| HPLC Pump | LPG-3400SD or DGP-3600SD or equivalent |
| HPLC Autosampler | WPS-3000TSL Analytical or equivalent |
| HPLC Column oven | TCC-3000SD or equivalent |
| HPLC Column | Polar Advantage II C18 150 × 4.6 mm, 5 μm or equivalent |
| HPLC Detector | VWD-3400RS or DAD-3000 or equivalent |
| Data system | Dionex Chromeleon version 7.0 or higher |

Both in-process and finished product samples were analyzed following test method TM9802-095. The bulk fermentation samples were prepared daily by pipetting 2.000 mL of sample into a 50 mL volumetric flask and diluting to volume with DHLA bulk fermentation diluent (0.1% w/v glutathione and N-acetyl-L-cysteine, 0.1% phosphoric acid v/v in acetonitrile/di-water (499:499:2)). The samples were filtered using syringe filters into HPLC vials, discarding the first 1-2 mL of filtrate. The finished product samples were prepared by pipetting 2.000 mL of sample into a 50 mL volumetric flask and diluting to volume with IPA. The samples were filtered using syringe filters into HPLC vials, discarding the first 1-2 mL of filtrate. Representative HPLC conditions are outlined in Table 7 below.

TABLE 7

| Component/Condition | Description |
|---|---|
| Column | Thermo Betasil C18 250 × 4.6 mm, 5 μm |
| Mobile phase A | 0.1 % Phosphate |
| Mobile phase B | ACN |
| Mobile phase C | Any alcohol (7.3) |
| Sample temp. | 5° C. |
| Run time | 12 minutes |
| Gradient Program | Gradient Table |

| Minute | % A | % B |
|---|---|---|
| 0 | 50 | 50 |
| 5 | 50 | 50 |
| 6 | 0 | 100 |
| 8 | 0 | 100 |
| 9 | 50 | 50 |
| 14 | 50 | 50 |

| | |
|---|---|
| Wavelength | 200 nm |
| Flow Rate | 1.0 mL/min |
| Sample Temp. | 5° C. |
| Column Temp. | 40° C. |
| Injection volume | 10 μL |
| Run Time | 14 minutes |

DHLA Fermentation Bulk Conversion HPLC Results.

Figure 3:
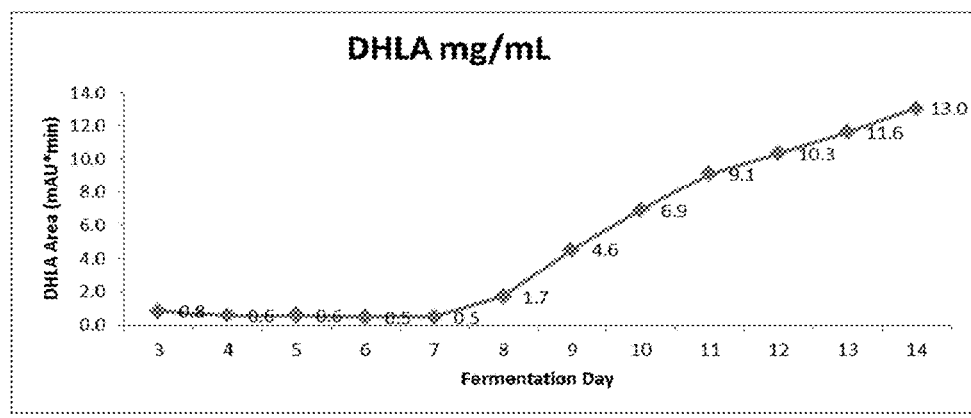
FIG. 3 depicts DHLA conversion in mg/ml produced over time in the bulk fermentation process and prior to addition of the olive oil.
Figure 4A:
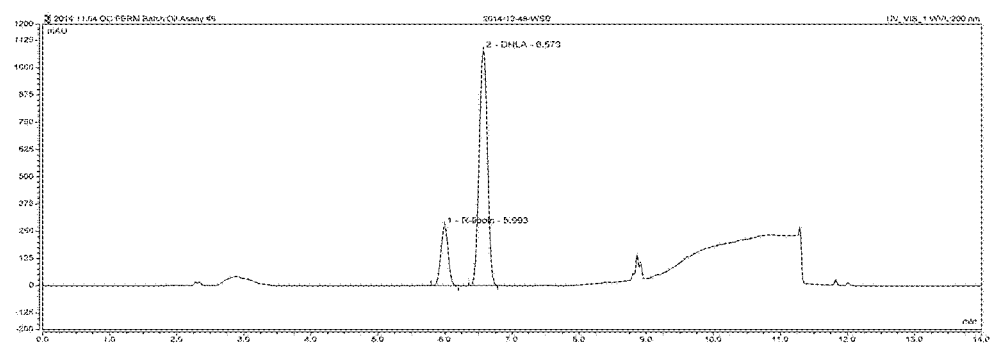
FIG. 4A depicts an HPLC chromatogram of the DHLA analytical standard.
Figure 4B:
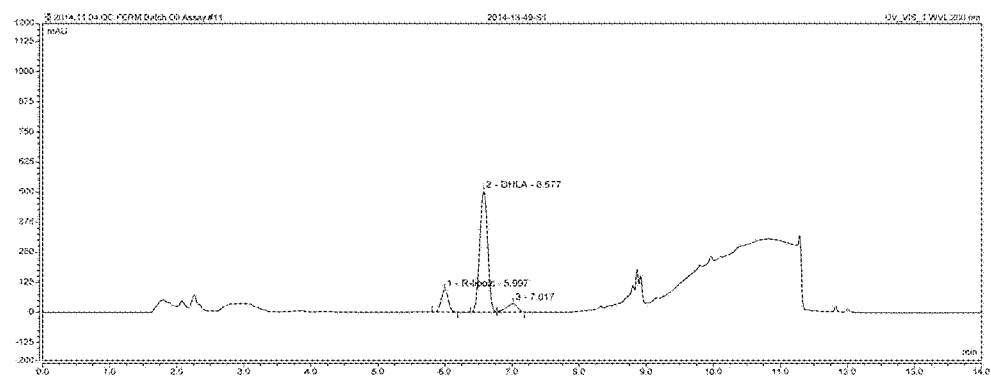
FIG. 4B depicts an HPLC chromatogram of a DHLA sample produced after 14 days of fermentation in accordance with one embodiment of the bulk fermentation process.

All samples performed daily were run on the HPLC to track the progression of DHLA conversion. Table 8 shows the results from each day up until processing (see also, line graph in FIG. 3). A DHLA standard was prepared daily and was injected at different volumes to form a curve in order to calculate the area of each peak. A continuous progression of DHLA conversion was observed each day after Day 7 (FIG. 3). FIG. 4A shows an HPLC chromatogram of the DHLA standard, and FIG. 4B shows an HPLC chromatogram of a DHLA sample produced after 14 days of fermentation.

TABLE 8

| Day | DHLA mg/ml | Rel. Area % |
|---|---|---|
| 3 | 0.8 | 6.8 |
| 4 | 0.6 | 4.9 |
| 5 | 0.6 | 4.9 |
| 6 | 0.5 | 4.1 |
| 7 | 0.5 | 4.1 |
| 8 | 1.7 | 13.6 |
| 9 | 4.6 | 34.0 |
| 10 | 6.9 | 49.8 |
| 11 | 9.1 | 59.1 |
| 12 | 10.3 | 67.6 |
| 13 | 11.6 | 74.1 |
| 14 | 13.2 | 78.8 |

(10) Olive oil is added to the batch at 60-100% total broth volume and water is added to the batch at 100% of broth volume.

(11) The batch is then mixed for NLT 45 minutes to extract DHLA oil from the aqueous broth.

(12) After mixing the broth is allowed to settle (or is centrifuged). Centrifugation will remove most residual cellular matter.

(13) After settling the olive oil layer containing DHLA is siphoned off.

In one embodiment, the isolated DHLA-containing oil layer can be assayed for DHLA content or antioxidant activity.

In one embodiment, the resulting olive oil layer containing DHLA can have a DHLA concentration of about 10 mg/ml. In another embodiment, the resulting olive oil layer containing DHLA can have a DHLA concentration of from about 5 mg/ml to about 20 mg/ml.

In another embodiment of the process, the bacterial cells may be lysed or inactivated by ethanol. That is, the cells can be inactivated, or killed. Stated in another way, the dead cells may be considered "once-living," Stated in another way, the lysed or inactivated cells may have a "cell status" wherein the CFU count is near zero (0) or essentially zero (0). Standard plate count with MRS agar is utilized to evaluate the viability of the cells.

Now turning to FIG. 1, the DHLA production process (10) is shown. The microbial broth made from the microbiological culture is added on 'Day Zero (0)' to reactor (20). After fermentation for about 48 hours, in the example microbial broth is fed with ingredients on 'Day 3' and including feedstock R-Lipoic Acid, and fermentation in reactor (20) is continued for 14-21 days. At 'Day 12' the fermentation batch is fed with the 'Day 12' ingredients, namely molasses, rice protein, yeast flakes, and Natamycin, in water. After fermentation is complete, the batch is adjusted to a pH of 2.0 and the olive oil (30) is added to the fermented microbial broth in reactor (20) for extraction of DHLA product. DHLA is isolated in the olive oil layer (40). The product of process (10) is a DHLA-containing oil layer (40).

Useful DHLA salts can include addition salts of carboxylic acids including sodium, potassium, magnesium, calcium, and the like.

Finally, it is now known that compounds derived from non-living sources lack DNA which is known to emit coherent light capable of nourishing and regenerating cellular DNA. When non-living source nutrients enter the cell they may induce DNA degradation and early cell death. Conversely, compounds derived from once living sources sustain cell DNA. Thus, it is believed that compounds derived from a once living source are more suitable for ingestion because they more closely approximate the compounds which are naturally ingested or produced within the body and thus they are safer, especially for long term use. One exemplary DNA source is Nucleocell nucleotides as used herein.

While various live probiotic organisms may be included in the microbiological culture media of the invention, in accordance with certain preferred embodiments, at least one probiotic organism can be selected from *Lactobacillus* species, *Bifidobacterium* species, *Enterococcus* species, generally accepted as safe (GRAS) *Streptococcus thermophilus*, and combinations thereof.

In accordance with another embodiment the process described herein ferments the lipoic acid with bacteria selected from the genus of any of the following bacteria: *Lactobacillus, Enterococcus, Pediococcus,* or *Bacillus*.

Examples of suitable *Lactobacillus* species (spp.) include, but are not limited to, *L. acidophilus, L. paracasei, L. fermentum, L. rhamnosus, L. johnsonii, L. plantarum, L. reuteri, L. salivarius, L. brevis, L. bulgaricus, L. helveticus, L. grasseri, L. casei, L. lactis,* and combinations thereof.

Examples of suitable *Enterococcus* species include, but are not limited to, *E. faceum, E. faecalis, E. durans, E. gallinarum,* and combinations thereof.

While various nutraceutical or nutritive agents can be utilized in the microbiological culture media of the invention, suitable nutraceutical or nutritive agents should contribute to the production of the desired beneficial compound as well as to the stability of the microbiological media. The particular nutraceutical or nutritive agent or agents utilized in the microbiological culture media will depend upon the beneficial compound to be derived. For example, if the beneficial compound to be derived from the microbiological culture media is stabilized dihydrolipoic acid (DHLA), the nutritive agent contained in the microbiological media may be tumeric rhizome (*curcuma longa*). In another preferred embodiment, the nutraceutical or nutritive agent utilized in the microbiological culture media may be a synthetic form or precursor of the beneficial compound to be derived or may be naturally occurring source of the beneficial compound, such as, for example, a plant or herb, which must be processed in order to isolate the beneficial compound.

In accordance with certain preferred embodiments of the invention, stabilized dihydrolipoic acid (DHLA) for use in a medicament or nutritional supplement is derived from a once living source. In particular, the stabilized DHLA compound can be derived from a microbiological culture media including at least one live probiotic organism, R-lipoic acid, and at least one nutraceutical or nutritive agent.

Synthetic sources of alpha-lipoic acid (ALA) generally include, in equal amounts, R-lipoic acid and S-lipoic acid. However, it has been discovered, that ALA containing S-lipoic acid possesses pro-inflammatory properties which results in the formation of undesirable compounds and may detract from the function of ALA. In practice, therefore, R-lipoic acid is utilized in the microbiological culture media and microbial fermentation broth.

While various nutraceuticals or nutritive agents can be utilized in the microbiological culture media of the invention, suitable nutraceuticals or nutritive agents should contribute to the production of DHLA as well as contribute to the stability of the microbiological media. In accordance with certain preferred embodiments, the nutraceutical or nutritive agent can be turmeric rhizome (*curcuma longa*).

The stabilized dihydrolipoic acid (DHLA) of the present invention may be prepared by dispersing a microbiological culture media including at least one live probiotic organism, R-lipoic acid and at least one nutritive agent in distilled water to form a microbial broth. The broth is then incubated at a predetermined or preferred pH range (e.g., about 8.0), and temperature range such as, for example, about 35° C. to about 40° C., for a select period of time such as, for example, about 72 to about 336 hours (i.e. about 3 to about 14 days) to induce probiotic activity. At the end of the incubation period, organic ethanol may be added to the broth to halt the probiotic activity and preserve the synthesized compounds. Thereafter, the product DHLA is separated from the broth by oil extraction and used to prepare a medicament or nutritional supplement.

While in the forgoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

What is claimed is:

1. A process for the production of dihydrolipoic acid (DHLA), or a salt thereof, comprising the steps of:
  (a) preparing a microbiological culture comprising at least one species of *Lactobacillus* spp., *Enterococcus* spp., *Pediococcus* spp., or *Bacillus* spp.;
  (b) treating an aqueous broth containing molasses, N-acetyl-L-cysteine, rice protein, nutritional yeast, sugar, one or more mineral salts, one or more nucleotides, and a first edible oil with the microbiological culture to form a microbial broth;
  (c) incubating the microbial broth at a temperature of about 35° C. to about 40° C. for at least about 48 hours;
  (d) feeding the microbial broth with R-lipoic acid, turmeric rhizome, N-acetyl-L-cysteine, glutathione, L-arginine, and NADH;
  (e) adjusting the pH to about 8.0;
  (f) incubating the microbial broth for at least about 10 days;
  (g) optionally feeding the microbial broth after the at least 12 days with molasses, rice protein, nutritional yeast, and natamycin;
  (h) optionally adjusting the pH to about 8.0;
  (j) incubating the microbial broth for at least about 2 days to about 9 days;
  (k) adjusting the pH to about 2.0;
  (l) adding a second edible oil in a volume of about 60-100% total microbial broth volume, and water in a volume of about 100% total microbial broth volume to form two layers;
  (m) mixing the edible oil layer and the aqueous layer to effect extraction of DHLA, or a salt thereof, into the edible oil layer; and (n) separating the edible oil layer containing DHLA, or a salt thereof.

2. The process of claim 1, wherein the microbiological culture comprises *L. casei* and *L. fermentum*.

3. The process of claim 1, wherein the incubating steps are carried out at a temperature of about 35° C. to about 40° C.

4. The process of claim 1, wherein R-lipoic acid is added to the microbial broth in an amount of about 20 g/kg to about 40 g/kg based on the total weight of the microbial broth.

5. The process of claim 1, wherein the edible oil layer containing DHLA, or a salt thereof, has a DHLA concentration of about 10 mg/ml.

6. The process of claim 1, wherein the first edible oil and the second edible oil can be the same or different, and the first edible oil and the second edible oil are each independently selected from the group consisting of olive oil, grape seed oil, sesame oil, borage oil, fish oil, sea buckthorne oil, flax oil, coconut oil, peanut oil, canola oil, jojoba oil, corn oil, palm oil, evening primrose oil, amaranth oil, safflower oil, soybean oil, sunflower oil, palm oil, cotton seed oil, almond oil, cashew oil, hazelnut oil, macadamia oil, pecan oil, pistachio oil, walnut oil, acai oil, blackcurrant oil, apricot oil, argan oil, artichoke oil, avocado oil, babassu oil, ben oil, borneo tallow nut oil, buffalo gourd oil, carob pod oil, coriander seed oil, false flax oil, hemp oil, kapok seed oil, lallemantia oil, meadowfoam seed oil, mustard oil, okra seed oil, *perilla* seed oil, pequi oil, pine nut oil, poppy seed oil, prune kernel oil, pumpkin seed oil, *quinoa* oil, ramtil oil, rice bran oil, tea oil, thistle oil, and wheat germ oil.

7. The process of claim 6, wherein the first edible oil and the second edible oil are each olive oil.

8. The process of claim 7, wherein the edible oil layer containing DHLA, or a salt thereof, has a DHLA concentration of about 10 mg/ml.

\* \* \* \* \*